United States Patent
Snow et al.

(10) Patent No.: US 6,498,249 B1
(45) Date of Patent: Dec. 24, 2002

(54) PHTHALOCYANINES WITH PERIPHERAL SILOXANE SUBSTITUTION

(75) Inventors: Arthur W. Snow, Alexandria, VA (US); James S. Shirk, Alexandria, VA (US); Eva M. Maya, Alexandria, VA (US); Richard G. S. Pong, Silver Spring, MD (US); Steven R. Flom, Temple Hills, MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 09/886,039
(22) Filed: Jun. 22, 2001
(51) Int. Cl.$^7$ .......................................... C07D 487/22
(52) U.S. Cl. ..................................................... 540/128
(58) Field of Search ........................................ 540/128

(56) References Cited

U.S. PATENT DOCUMENTS

| | | | |
|---|---|---|---|
| 3,963,744 A | 6/1976 | Smith et al. | 260/314.5 |
| H477 H | 6/1988 | Barger et al. | 540/140 |
| 5,805,326 A | 9/1998 | Snow et al. | 359/241 |

OTHER PUBLICATIONS

Snow, Shirk, Pong, Oligooxyethylene Liquid Phthalocyanines, Journal of Porphyrins and Phthalocyanines, 2000, p.518–524.
Maya, Snow, Shirk, Flom, Pong, Roberts, Silicone Substituted Phthalocyanines for Optical Limiting Applications, presented at 221st National American Chemical Society Meeting, San Diego, CA, Apr. 5, 2001.
Nalwa, Shirk, Phthalocyanines: Properties and Applications:, vol. 4, C.C. Lenzoff and A.B.P. Levers, editors, VCH Pub. Inc., N.Y., 1996 from Chapter 3.
George, Snow, Shirk, Barger, The Alpa Substitution Effect on Phthalocyanine Aggregation, J. Porphyrins and Phthalocyanines, vol. 2, 1–7, 1998.
Barrett, Fry, Linstead, Phthalocynines and Associated Compounds, Macromolecules, vol. 17, 1614, 1984.
Holohan, George, Barrie, Monofunctional Polydimethylsiloxane Oligomers for Graft Copolymerisation, Micromolecules, vol. 195, 1965 (1994).
Gurek, Bekaroglu, Octakis (alkylthio)–Substituted Phthalocyanines and their Interatctions with Silver (I) and Palladium (II) Ions, J. Chem. Soc. Dalton Trans., vol. 1994, 1419 (1993).
Iwatsu, Kobayashi, Uyeda, Solvent Effects on Crystal Growth and Transformation of Zinc Phthalocyanine, J. Phys. Chem., vol. 84, 3223 (1980).
Yamashita, Hayashi, Organic Molecular Beam Deposition of Metallophthalocyanines for Opto–electronics Applications, Advanced Materials, vol. 8, 791 (1996).
Flom, Shrik, Lindle, Bartoli, Kafafi, Pong, Snow, Mechanisms of the Nonlinear Optical Response in Tetrakis (cumylphenoxy) Phthalocyanines, Materials Research Society, vol. 247, 271 (1992).
McKeown, Phthalocyanine–containing Polymers, J. Materials Chemistry, vol. 10, 1979 (2000).
Brewis, Clarkson, Goddard, Helliwell, Holder, McKeown, Silicon Phthalocyanines with Axial Dendritic Substituents, Angew Chem. Int. Ed., vol. 37, 1092 (1998).
Kane, Sullivan, Kenney, The Nuclear Magnetic Resonance Spectra and the Electronic Spectra of Some Silicon and Germanium Phthalocyanines, Inorg. Chem., vol. 9, No. 6, 1445 (1970).
Schouten, Warman, Haas, Van Nostrum, Gelinck, Nolte, Copyn, Zwikker, Engel, Hannack, Chang, Ford, The Effect of Structural Modifications of Charge Migration in Mesomorphic Phthalocyanines,J. Am. Chem. Soc., vol. 116, 6880 (1994).
Kimura, Nakada, Dendritic Metallophthalocyanines: Synthesis and Characterization of a Zinc (II) Phthalocyanine [8]3–Arborol, Chem. Comm., vol. 1557, 1215 (1997).
Brewis, Helliwell, McKeown, Reynolds, Shawcross, Phthalocyanine–centered Aryl Ether Dendrimers with Oligo(ethyleneoxy) Surface Groups, Tetrahedron Lett., vol. 42, 813 (2001).
McKeown, Phthalocyanine Materials: Synthesis, Structure and Function, Cambridge University Press, Edinburgh, (1998) pp. 62–86.
George, Snow, Phthalocyanine Glasses, Chem. Mater., vol. 6, 1587 (1994).
Snow, Griffith, Marullo, Synthesis and Characterization of Heteroatom–Bridged Metal–Free Phthalocyanine Network Polymers and Model Compounds, Macromolecules, Aug. 1984, 1614–1624.
Brewis, Hassan, Li, Makhseed, McKeown, Thompson, The Synthetic Quest for 'Splendid Isolation' Within Phthalocyanine Materials, J. Porphyrins Phthalocyanines, vol. 4, 460 (2000).
Maya, Shirk, Snow, Roberts, Peripherally–substituted Polydimethylsiloxane Phthalocyanines: A Novel Class of Liquid Materials, Chem. Commun., 615 (2001).

*Primary Examiner*—Richard L. Raymond
(74) *Attorney, Agent, or Firm*—John J. Karasek; Rebecca L. Forman

(57) ABSTRACT

The present invention is phthalocyanine compounds with peripheral siloxane substitution, as well as methods for making these compounds and various uses thereof, having the basic structure:

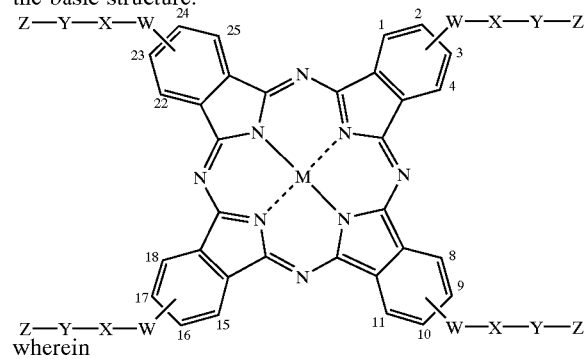

wherein

—W—X—Y—Z are peripheral groups comprising individual W, X, Y, and Z subgroups;

W is a linkage represented by the formula: —D—$(R^1)_{0,1}$—, where D=S or O;

X is: —$(CH_2)_n$—, n=2 to 8;

Y is a siloxane chain;

Z is an aryl or alkyl terminal cap;

M is two protons or a metal ion;

and forms a transparent film of high optical quality with large nonlinear absorption and thermal refraction, free of scattering from solid or liquid crystalline domains making them highly suitable for use as the active component in thin films, protective eye wear, and optical data storage applications.

27 Claims, 2 Drawing Sheets

PHTHALOCYANINES WITH PERIPHERAL SILOXANE SUBSTITUTION

BACKGROUND OF THE INVENTION

1. Field of the Invention

The present invention relates to new compounds that are a combination of covalently linked phthalocyanine and linear siloxane polymeric structures having a unique and novel combination of optical and rheological properties which are useful in protective eye wear, nonlinear optical devices and for optical data storage applications.

2. Description of the Related Art

Previously developed phthalocyanine materials have not possessed the handling and processing characteristics of a single-component fluid coupled with an optical transparency, nonlinear optical absorption and refraction, chemical stability and moisture resistance. These are desirable characteristics for use as thin films in nonlinear optical and optical recording applications. Known methods for preparing phthalocyanines as thin films include vacuum deposition (sublimation, molecular beam, laser desorption), spraying or casting of a fine suspension or solution, Langmuir-Blodgett transfer, mechanical abrasion, and dispersion in a binder. The transparent thin film is a highly desirable physical form for these materials as it allows utilization of the chromophore in optical applications such as optical limiting and optical recording media which typically involve as material response to irradiation with a laser.

The deposition method, optical quality, and stability of a phthalocyanine film are determined by the molecular structure and properties of the material. Without peripheral substituents, phthalocyanine compounds are microcrystalline and relatively insoluble. Thin film preparation by vacuum deposition or high pressure abrasive techniques must frequently be accompanied by high temperatures. The microcrystalline character and the presence of different crystalline polymorphs contribute to optical scattering. These effects diminish the transparency of the phthalocyanine film. Temperature variation and exposure to chemical vapors (including water) causes conversions between different crystalline forms further diminishing the quality of the film. (See M. S. Mindorff and D. E. Brodie, *Can. J. Phys.,* 59, 249 (1981); F. Iwatsu, T. Kobayashi and N. Uyeda, *J. Phys. Chem.,* 84, 3223 (1980); F. W. Karasek and J. C. Decius, *J. Am. Chem. Soc.,* 74, 4716 (1952))

When peripheral substituents are bonded to the phthalocyanine, molecular packing efficiency and crystallinity are reduced, and the resultant materials may be soluble in a variety of solvents. Film forming techniques involving the use of solvents, such as simple evaporation methods and Langmuir-Blodgett transfer techniques, are feasible processing methods. However, many peripherally substituted phthalocyanines do not form films of good transparent optical quality. The peripheral groups need to be large in size and preferably of mixed isomer substitution to be effective. While crystalline packing is hindered by the presence of peripheral substituents, there are strong attractive van der Waal forces at work between the planar faces of phthalocyanine rings which result in the constituent molecules aggregating into ordered domains. These domains, if large enough, cause optical scattering which strongly deteriorates the transparency and optical quality of thin films. (See T. Kobayashi, in *Crystals: Growth Properties and Applications,* N. Karl, editor, Springer-Verlag, New York, Vol 13 (1991) pp. 1–63; A. Yamashita and T. Hayashi, *Adv. Mater.,* 8, 791 (1996)).

The interaction between adjacent phthalocyanine rings in an aggregate also results in a strong electronic perturbation of the molecular structure and a broadening of its absorption in the visible spectrum. This interaction in many cases detracts from the sought after nonlinear optical properties. (See S. R. Flom, J. S. Shirk, J. R. Lindle, F. J. Bartoli, Z. H. Kafafi, R. G. S. Pong and A. W. Snow, in *Materials Res. Soc. Proc.,* Vol. 247, (1992) pp 271–276).

Control of phthalocyanine aggregation is important first to reduce the ordered domain size below a threshold where optical scattering occurs and second to reduce the pertubation of the phthalocyanine electronic structure to a level where spectral broadening and excited state lifetime shortening do not seriously diminish the nonlinear optical absorption of the phthalocyanine chromophore. The former is critical since optical transparency is required for a device of the current invention to function. For sufficient control of optical scattering, the ordered molecular domain size must be smaller than the light wavelength of application interest (usually in the 350 to 1500 nm range). The latter is less critical, but significant improvement in nonlinear optical properties can be realized if aggregation can be reduced to dimer formation or less.

Aggregation can be totally eliminated by blocking the co-facial approach of phthalocyanine rings by axial substitution onto metal ions complexed in the phthalocyanine cavity. (See N. B. McKeown, *J. Mater. Chem.,* 10, 1979 (2000); M. Brewis, G. J. Clarkson, V. Goddard, M. Helliwell, A. M. Holder and N. B. McKeown, *Angew. Chem. Int. Ed.,* 37, 1092 (1998); A. R. Kane, J. F. Sullivan, D. H. Kenny and M. E. Kenney, *Inorg. Chem.,* 9, 1445 (1970)). However, this approach is limited to a small number of tetravalent octahedrally coordinating metals such as silicon. For reasons discussed below, the nonlinear optical properties of this small group of metallophthalocyanines are not particularly useful. (See H. S. Nalwa and J. S. Shirk, in *Phthalocyanines: Properties and Applications,* C. C. Leznoff and A. B. P. Lever, editors, VCH Publishers, Inc., New York (1996) Ch. 3).

Another approach to aggregation control is to utilize very large peripheral substituent groups that hinder the co-facial approach of phthalocyanine rings. Classes of such peripheral substituents are flexible oligomers (see D. Guillon, P. Weber, A. Skoulios, C. Piechocki and J. Simon, *Molec. Cryst. Liq. Cryst.,* 130, 223 (1985); P. G. Schouten, J. M. Warman, M. P. Dehaas, C. F. van Nostrum, G. H. Gelineck, R. J. M. Nolte, M. J. Copvyn, J. W. Zwikker, M. K. Engel, M. Hannack, Y. H. Chang and W. T. Ford, *J. Am. Chem. Soc.,* 116, 6880 (1994)), dendrimers (see M. Kimura, K. Nakada, Y., *Chem. Comm.,* 1997, 1215; M. Brewis, B. M. Hassan, H. Li, S. Makhseed, N. B. McKeown and N. Thompson, *J. Porphyrins Phthalocyanines,* 4, 460 (2000); M. Brewis, M. Helliwell, N. B. McKeown, S. Reynolds and A Shawcross, *Tetrahedron Lett.,* 42, 813 (2000)), and capping groups (see D. D. Dominguez, A. W. Snow, J. S. Shirk and R. G. S. Pong, *J. Porphyrins and Phthalocyanines,* 5, 582 (2001)). Examples of these three types of peripheral groups have had limited success in reducing aggregation. In many cases where the large peripheral groups have significant structural symmetry and uniformity of size, liquid crystal formation with its consequent optical scattering has resulted. (See N. B. McKeown, *Phthalocyanine Materials: Synthesis, Structure and Function,* Cambridge University Press, Edinburgh (1998) pp. 62–86). The liquid crystallinity has been avoided by utilizing peripheral groups with irregular symmetry combined with hydrogen bonding functional groups (see R. D. George and A. W. Snow, *Chem. Mater.,* 6, 1587 (1994)) or using a polydispersity of peripheral group chain lengths (see A. W. Snow, J. S. Shirk and R. G. S. Pong, *J. Porphyrins Phthalocyanines,* 4, 518 (2000)). In the former case an epoxy-amine chemistry was utilized and a non-birefringent organic glass was obtained, while in the latter case polyethylene oxide chemistry was employed and an isotropic liquid was obtained. The organic glass or liquid has very favorable melt processing characteristics.

Another requirement on the nature of the peripheral group is that it must be chemically inert toward the metal ions complexed in the phthalocyanine cavity. Many of the metal ions that instill very useful nonlinear optical properties to the phthalocyanine chromophore are moderately labile and may be removed from the phthalocyanine cavity by competing complexing agents. This is particularly true of the heavy metal ions. In previous work with phthalocyanine compounds having polyethylene oxide peripheral groups, it was found that the ethylene oxide structure was a strong enough competitor in complexing with a lead ion and remove it from the phthalocyanine cavity (E. M. Maya, A. W. Snow, J. S. Shirk, S. R. Flom, R. G. S. Pong and G. L. Roberts, "Silicone Substituted Phthalocyanines for Optical Limiting Applications" presented at 221st National American Chemical Society Meeting, San Diego, Calif., Apr. 5, 2001). To be useful for the current invention, the peripheral groups must not behave in this manner.

Regarding specific instances of tethering a siloxane group to a peripheral site of a phthalocyanine compound, only one example is known (U.S. Pat. No. 3,963,744). In this instance, the siloxane group is a tris(trimethylsiloxy) silylalkyl structure which is connected through an alkylsulfamide linkage to the phthalocyanine periphery. This material is claimed to be compatible with cross-linked silicone polymers for the purpose of acting as a dye or a pigment. This tris(trimethylsiloxy)silylalkyl structure is compact (highly branched with short-chains) and nonlinear. A compound with these characteristics does not form useful transparent thin films. Conversely, the present invention teaches linear polysiloxane structures. This linear quality is a critical feature in thin film processing and nonlinear optical property enhancement.

Finally, the nonlinear optical properties of phthalocyanine materials are strongly dependent on the identity of the species complexed within its cavity. While this species may range from two protons to a wide variety of transition and main group metal ions, phthalocyanines with complexed heavy metal ions such as tin, bismuth, mercury, indium, tellurium, and particularly lead display the strongest nonlinear optical properties (see U.S. Pat. No. 5,805,326; H. S. Nalwa and J. S. Shirk, in *Phthalocyanines: Properties and Applications,* Vol. 4, C. C. Leznoff and A. B. P. Lever, editors, VCH Publishers, Inc., New York (1996) Ch. 3). In the divalent state, these metal ions do not coordinate to axial ligands. Thus, such ligands cannot be utilized to block aggregation. Many of these metal ions are labile and can be easily displaced by competing chelating structures. This problem is particularly acute with the polyethylene oxide structure where the oxygen sites in this polymer chain coordinate with the metal ion resulting in its consequent removal from the phthalocyanine cavity and diminishment of nonlinear optical properties.

SUMMARY OF THE INVENTION

Accordingly, one objective of the present invention is to provide a modified phthalocyanine that forms a transparent film of high optical quality, free of scattering from solid or liquid crystalline domains.

Another objective of the present invention is to provide a phthalocyanine material that has been modified so that it is processable as an isotropic liquid or glass. Such processing includes: filling confined very small spaces (0.01 to 100 micron) by capillary action; mechanically producing a film by shearing between two flat surfaces; and casting a film by solvent evaporation.

A further objective of the present invention is to produce phthalocyanine films that display large nonlinear optical absorptions suitable for use in optical limiting applications.

A further objective of the present invention is to produce phthalocyanine films that have a large nonlinear thermal refraction to complement the nonlinear photochemistry in optical limiting applications.

A further objective of the present invention is to provide a phthalocyanine material that has been modified so that it is useful in the following applications: as a protective element in an optical limiting component of direct view optical goggles, periscopes, gun sights, and binoculars; as the active element in laser intensity control and passive laser intensity noise reduction devices; as an optical switching element in an optical communications circuit; and as a component in compact disks, DVD's, optical cache memories, and holographic memories.

These and other objectives of the present invention are accomplished through covalent bonding of siloxane oligomer structures of appropriate number, chain length and size distribution to connecting sites at the periphery of the phthalocyanine ring structure and by complexation of appropriate heavy metal ions in the phthalocyanine cavity.

BRIEF DESCRIPTION OF THE DRAWINGS

A more complete appreciation of the invention will be readily obtained by reference to the following 'Detailed Description of the Preferred Embodiments' section and these drawings.

DETAILED DESCRIPTION OF THE PREFERRED EMBODIMENTS

Figure 1:
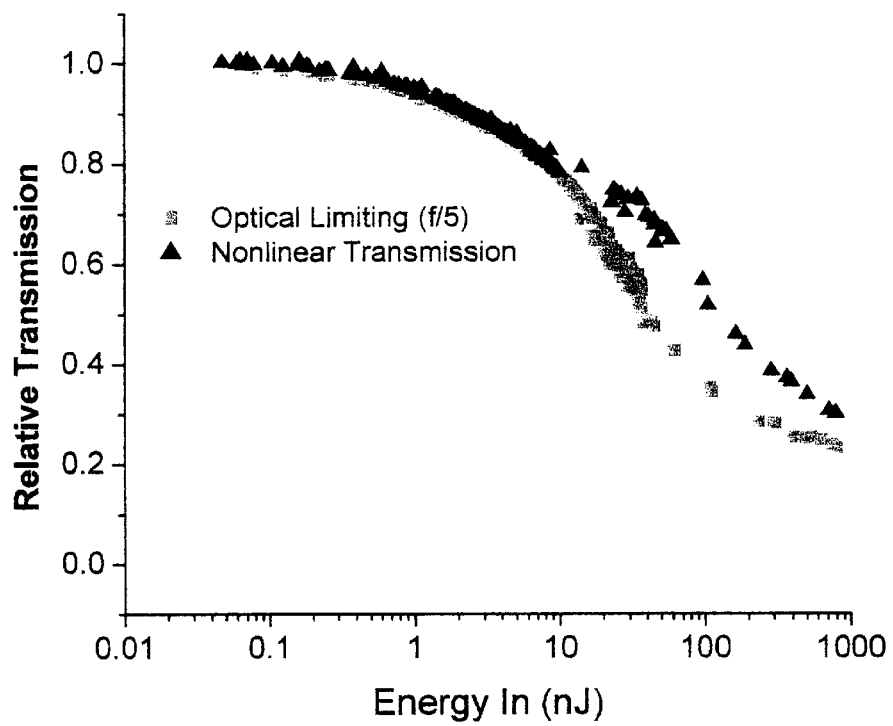
FIG. 1 is a graph showing the nonlinear transmission and optical limiting of a 4.2 $\mu$m thick sample of pure liquid PbPc(PDMS$_{10}$)$_4$.

Silicones have unique and useful properties as fluids and rubbers. Phthalocyanines have unique properties for optical and electronic applications. Due to mutual incompatibility of silicones and phthalocyanines, a combination of the unique and useful properties described above cannot be achieved by simply blending these materials. However, this invention achieves a coupling of silicones and phthalocyanine rings via covalent bonding into a single molecular substance which results in a unique combination of the useful properties of each component. There are alternative methods described herein for achieving this coupling of silicone chains to phthalocyanine rings.

The phthalocyanine material of the subject invention is described by the general structural formula below. The central phthalocyanine substructure is the chromophore wherein resides the nonlinear optical absorption of visible light. Critical features to the general structure that control this and other important material properties are the nature of the W, X, Y, Z peripheral group substructures and the species M complexed in the cavity.

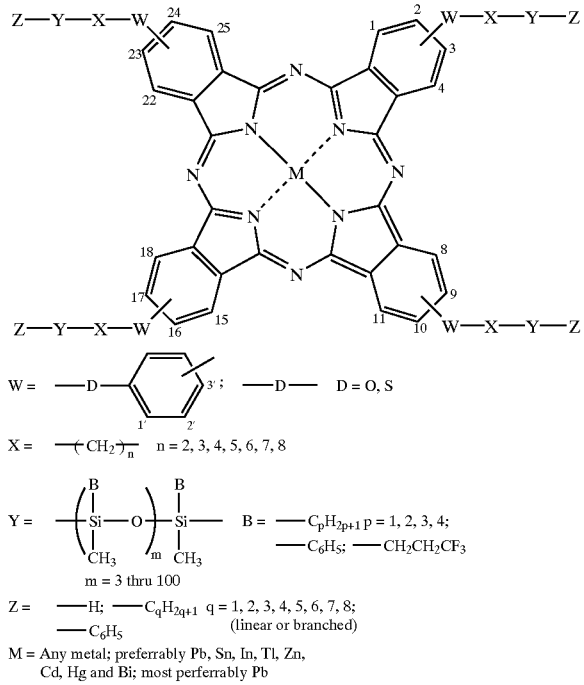

In the phthalocyanine structure, the numbered positions on the benzo ring substructures indicate the peripheral positions where the group(s) W, X, Y, and Z may be covalently bonded. Each of the four benzo ring substructures may accommodate 0, 1 or 2 W—X—Y—Z substituents with the preferred arrangement being one W—X—Y—Z substituent on each benzo ring substructure. There are four possible positions for peripheral substitution on each of the benzo ring substructures. All combinations are practicable, but the preferred arrangements are those of low symmetry so that the phthalocyanine compound is a mixture of geometric isomers. This mixed isomer character is more effective in inhibiting crystalline packed arrangements.

The peripheral group W—X—Y—Z is composed of four subunits with each having possible structural variations. The variations are primarily determined by the synthetic route used in preparing the phthalocyanine as described below, and the preferred arrangements are determined by both the facility of the synthesis route as well as the desired physical properties.

The W component of the group W—X—Y—Z is an ether or thioether linkage, and is either diaryl or arylalkyl. This is determined by the nitro displacement nucleophilic aromatic substitution reaction in the synthesis in which a phenol or an alcohol or corresponding sulphur analog may be used. The diaryl ether or thioether linkage is preferred because it has better photo-oxidative stability. When the phenol or thiophenol is used to make the diaryl linkage, there are three possible linkage sites on the phenylene group (1', 2', 3' or ortho, meta and para respectively) to which the X subgroup is bonded. While all as well as mixtures are practicable, the 1' (or ortho) position is preferred. This occurs for synthesis as well as property reasons. Substitution at the ortho position causes the W—X—Y—Z group to turn back toward the face of the phthalocyanine ring resulting in a steric hindrance caused by cofacial aggregation. This mechanism for depressing aggregation has a highly desirable effect on the nonlinear optical properties.

The X component is a variable length alkane chain. Its presence results from the hydrosilylation coupling reaction between a terminal olefin and a silylhydride terminated siloxane. In principle, an alkane of any chain length may perform this function and variations incorporating chain branching or heteroatoms are workable. The preferred structure for subgroup X is a short chain length with the optimum preference being a trimethylene group. This group is the most synthetically facile. Its short chain length also has a minimal diluting effect on the thermal refractive optical property associated with the silicone structure (subgroup Y).

The Y component is a siloxane chain of variable length. This substructure is responsible for the liquid or glassy character of the phthalocyanine material and for the exceptionally large thermal refractive nonlinear optical effect. There are three important variables within this substructure: the length, m, of the siloxane chain, the dispersity of the siloxane chain length, and the identity of the pendent group B. The siloxane chain length correlates with the glass transition temperature (Tg) and determines whether the material will be a glass or a liquid. Very short chains (3 or 4 units) correlate with a Tg above ambient, while longer ones (>6 units) depress the Tg below room temperature. For liquid phthalocyanine materials, the viscosity correlates with the siloxane chain length; initially decreasing with increasing chain length in opposition to the influence of the phthalocyanine substructure, then increasing with further chain length reflecting the effect of the siloxane molecular weight. The longer the chain length (the greater the volume fraction of the Y component), the more this phthalocyanine material's rheology and morphology resemble the pure siloxane material. The longer chain lengths also reduce phthalocyanine aggregating tendency by steric hindrance. However, the phthalocyanine structure's volume fraction must remain significant (in the approximate range from a high of 25% to a low of 1%, which correlates with a siloxane chain length between 3 and 100) if the nonlinear optical properties associated with this chromophore are to be utilized in a thin film physical form. In general, the preferred chain lengths range from 7 to 28 units. A polydispersity of siloxane chain length is a variation about an average chain length. While the current invention may be practiced with either a monodisperse or polydisperse siloxane chain, polydispersity is beneficial in that its breadth reduces a tendency for organized molecular packing which may result in liquid crystal formation. The synthesis method for preparation of the silylhydride terminated siloxane intermediates yields a polydisperse product, utilized without fractionation in the current invention.

The identity of the pendant group B on the siloxane chain is a very important variable in that this feature offers a method of controlling the refractive index of the phthalocyanine material. The preferred identity is methyl for reasons of availability of precursors, synthesis facility and associated useful optical, physical and processing properties. However, the phthalocyanine material refractive index may be either increased or decreased by substituting the phenyl or 3,3,3-trifluoropropyl respectively for the methyl group in a fraction or all of the pendant B groups.

The Z component is a terminal or capping group on the free end of the siloxane chain. It is typically an inert alkyl group from the alkyl lithium initiator used in preparing the siloxane polymer from the cyclic trimer by anionic polymerization. This is the preferred embodiment as it confers a long term stability and processability to the phthalocyanine material. However, this terminal group may also be a reactive functional group such as a silylhydride. In this case, the phthalocyanine compound may couple with other or similar functional groups to generate network structures. The phthalocyanine compound may also bond to surfaces by reaction of the silylhydride group.

The M component is either a metal ion or two protons. The identity of the metal ion has a very important influence on the nonlinear optical absorption of the phthalocyanine chromophore. Previous teaching (U.S. Pat. No. 5,805,326) has demonstrated that heavy metal ions, particularly lead, are the preferred embodiments. The invention will function with other metal ions as well as the two protons complexed in the phthalocyanine cavity although the efficiency in the optical limiting application is not as high.

The synthesis of phthalocyanine compounds is well known to those skilled in the art. The following references provide a comprehensive review: D. Whöle, G. Schnurpfeil and G. Knothe, *Dyes and Pigments,* 18,91–102(1992); A. B. P. Lever, *Advances in Inorganic and Radiochemistry,* 58,27–114 (1965); C. C. Leznoff and A. B. P. Lever (editors), *Phthalocyanines: Properties and Applications,* VCH Publishers, Inc., Vol. 1 (1989); F. H. Moser and A. L. Thomas, *The Phthalocyanines,* CRC Press, Inc., Vols. 1 and 2 (1983); B. D. Berezin, *Coordination Compounds of Porphyrins and Phthalocyanines,* John Wiley & Sons (1981); N. B. McKeown, *Phthalocyanine Materials: Synthesis, Structure and Function,* Cambridge University Press (1998). Specific details for many particular phthalocyanine compounds may be found in the many articles cited by the above reviews.

The phthalocyanine materials of the subject invention are unique in that linear siloxane polymers are tethered to the periphery of the phthalocyanine structure to obtain very novel and useful properties (i.e. intrinsic liquid character, large refractive index—temperature dependence, isotropic thin film formation, and chemical inertness) that have not been previously achieved by other peripherally bonded structures. In the prior art, the only instance of tethering a siloxane group at the periphery of a phthalocyanine ring involved a tris(trimethylsiloxy)silylalkyl group attached through a sulfamide linkage to the phthalocyanine periphery (U.S. Pat. No. 3,963,744). This highly branched and very symmetrical group has a highly different chemistry, synthesis method, properties and purpose from the linear long chain siloxane polymers used in the present invention.

The synthesis used in the present invention consists of a series of reactions depicted below:

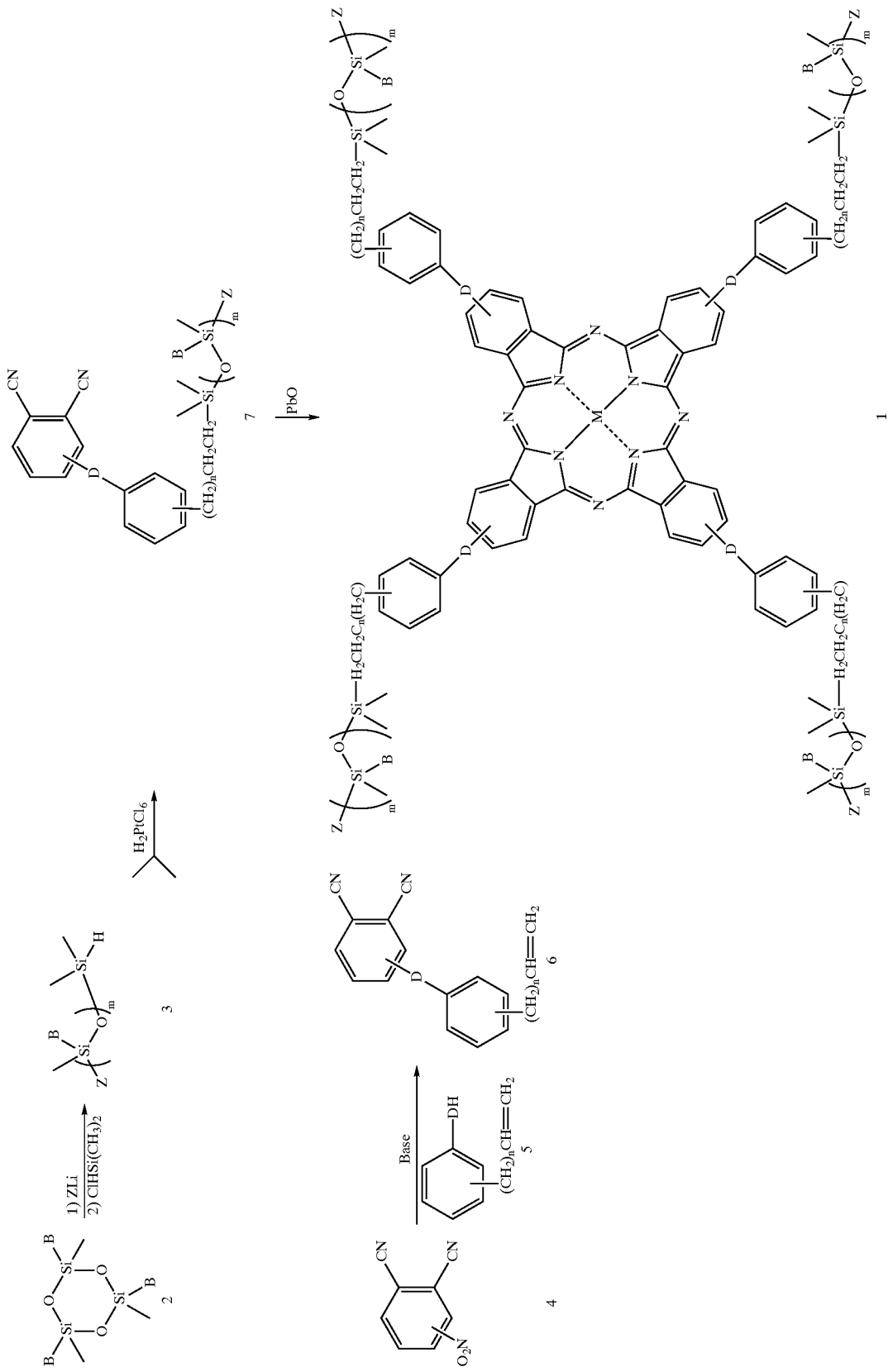

The first step is preparation of the silylhydride terminated siloxane polymer, 3, by anionic polymerization of the cyclotrisiloxane, 2, following a published procedure (see A. T. Holohan, M. H. George, J. A. Barrie and D. G. Parker, *Macromol. Chem. Phys.*, 195, 2965 (1994)). The siloxane chain length is determined by the monomer:alkyl lithium initiator molar ratio. The product distribution is narrow but not monodisperse. The identity of the alkyl capping group, Z, is determined by selection of alkyl lithium initiator. The silylhydride terminal group is supplied by the dimethylchlorosilane termination reagent. The pendant group, B, may be an alkyl group, phenyl group or a haloalkyl group and is determined by selection of the cyclotrisiloxane monomer, 2.

The second step is preparation of the olefin terminated alkyl substituted phthalonitrile intermediate, 6, by a nucleophilic aromatic nitro displacement reaction between the nitrophthalonitrile, 4, and the terminal olefin substituted alcohol or phenol, or corresponding sulphur analog, 5. There are many possibilities for structural variation in these reagents. The nitro group in 4 may be substituted at the 3- or 4-position. Substitution at the 3-position has been shown to reduce aggregation tendency in the analog phthalocyanine compound (R. D. George, A. W. Snow, J. S. Shirk and W. R. Barger, *J. Porphyrins and Phthalocyanines*, 2, 1–7 (1998)). For reagent 5, a terminal olefin substituted alkylphenol or alkylthiophenol is the preferred embodiment. The use of terminal olefin substituted alcohols, such as allyl alcohol, is practicable, however, the reaction yields are lower and the phthalocyanine analog compound has less stability compared with using the phenol. While practically any phenol or thiophenol with an olefin terminated alkyl substituent is preferred, a most preferred embodiment for reagent 5 is 2-allylphenol. This precursor is readily available, synthesis yields are good, phthalocyanine analog stability is good, and phthalocyanine aggregation tendency is lowered. The volume fraction of this hydrocarbon linkage substructure is significantly lower when compared with using phenols with larger olefin terminated alkyl groups. Details of the preparation of this 4-(2-allylphenoxy)phthalonitrile key intermediate are given in Example 1.

The third step is preparation of the polysiloxane substituted phthalonitrile intermediate, 7, by a hydrosilylation coupling reaction between the olefin terminated phthalonitrile, 6, and the silylhydride terminated siloxane polymer, 3. This reaction requires a trace amount of a hydrosilylation catalyst, such as chloroplatinic acid. (see Examples 2 and 3)

The fourth step is conversion of the siloxane substituted phthalonitrile, 7, to the corresponding phthalocyanine, 1. Two frequently used conditions employing hydroquinone (see A. W. Snow, N. P. Marullo, and J. R. Griffith, *Macromolecules*, 17, 1614 (1984)) or lithium pentoxide (P. A. Barret, D. A. Frye, and R. P. Lindstead, *J. Chem. Soc.*, 1938, 1157) as coreactants were not successful. The use of DBU (1,8-diazabicyclo[5.4.0]undec-7-ene) or dimethylaminoethanol/metal salt as the coreactants are practicable. However, the preferred route is to use lead (II) oxide as the coreactant. This yields the desired lead phthalocyanine, 1 M=Pb, is good yield (Examples 5 and 6). This lead phthalocyanine may be transformed to the corresponding metal-free phthalocyanine, 1 M=$H_2$, by treatment with a small amount of acid (Example 8). A wide variety of other metals may then be introduced into the phthalocyanine cavity by treatment of the metal-free phthalocyanine with a solution of a basic salt (e.g. an acetate) of the desired metal.

An alternate but less preferred synthetic route to the desired siloxane substituted phthalocyanine, 1, is to reverse the order of the third and fourth steps by converting the olefin terminated alkyl substituted phthalonitrile intermediate, 6, to its corresponding tetraallylphenoxy phthalocyanine (Examples 4 and 7) then couple the silylhydride terminated siloxane polymer, 3, to this tetraallylphenoxy phthalocyanine to yield the siloxane substituted phthalocyanine, 1, using a non-acidic heterogeneous catalyst, such as platinum-divinyl tetramethyldisiloxane. This route requires a large excess of the silylhydride terminated siloxane polymer, 3, in the final step to insure total functionalization of the allylphenoxy phthalocyanine which makes the purification of the final compound much more difficult.

The polysiloxane substituted phthalocyanines of the current invention, with the peripheral group molecular structure falling within the ranges specified for the W—X—Y—Z component of the general structure shown above, display characteristics of a very high quality optically transparent film. Observations and physical measurements on phthalocyanine materials prepared in Examples 5,6 and 8 verify these characteristics. When these materials are examined under high optical magnification (600 X) between crossed polarizers, no birefringence is observed. This is a sensitive test to directly diagnose the existence of very small molecularly ordered anisotropic domains with liquid or solid crystalline character. This observation is further supported by noting in the region of the optical spectrum where no phthalocyanine absorption occurs (900–1200 nm), the base line is virtually flat. As a further obsevation, no visually observed scattered light when the film is under intense laser irradiation. This is a clear indication that the polysiloxane peripheral groups are successful in prevention of formation of ordered domains whose dimension is comparable to the visible light wavelength or larger.

Quantitative measurements have also been made on the dimerization formation constant which is a parameter by which aggregating tendency can be assessed. The results are presented in Table 1 for the polysiloxane substituted phthalocyanine compounds of Examples 5 ($PbPc(PDMS_{10})_4$ and 8 ($H_2Pc(PDMS_{10})_4$ along with comparative data for the respective cumylphenoxy substituted phthalocyanines ($PbPc(CP)_4$ and $H_2Pc(CP)_4$).

TABLE 1

| Dimerization Formation Constants in Solution | | | |
|---|---|---|---|
| $H_2Pc(CP)_4$ | $K_D = 7000\ M^{-1}$ | $H_2Pc(PDMS_{10})_4$ | $K_D = 31\ M^{-1}$ |
| $PbPc(CP)_4$ | $K_D = 400\ M^{-1}$ | $PbPc(PDMS_{10})_4$ | $K_D = 2\ M^{-1}$ |

These measurements clearly demonstrate that the polysiloxane substituent relative to the cumylphenoxy hydrocarbon substituent reduces the tendency of the phthalocyanine to aggregate by a factor of at least 15 in both the metal-free and lead substituted analogs.

Another very critical physical characteristic conferred on the phthalocyanine material by the polysiloxane peripheral group is that of facile processability. Depending on the glass transition temperature, this peripheral group renders the phthalocyanine an amorphous isotropic glass or liquid. As such these materials can be processed as melts by simple application of heat to regulate the viscosity. The phthalocyanines of the Examples 5, 6 and 8 have respective Tg's of 3, 10 and −3° C. These materials are room temperature liquids and may be processed as thin films of very uniform and precisely controlled thickness by using capillary action to fill short pathlength (1 to 50 micron) flat optical cells. Smaller confined spaces down to 0.01 micron may also be filled by capillary action.

These polysiloxane phthalocyanines may also be processed by mechanically shearing a film between two optical surfaces. Alternately, the phthalocyanine materials of this invention are soluble in a variety of solvents and the simple generation of films by solvent casting or spraying and evaporation is a practicable technique. Blending these phthalocyanines in polymers is another method of film preparation.

Figure 2:
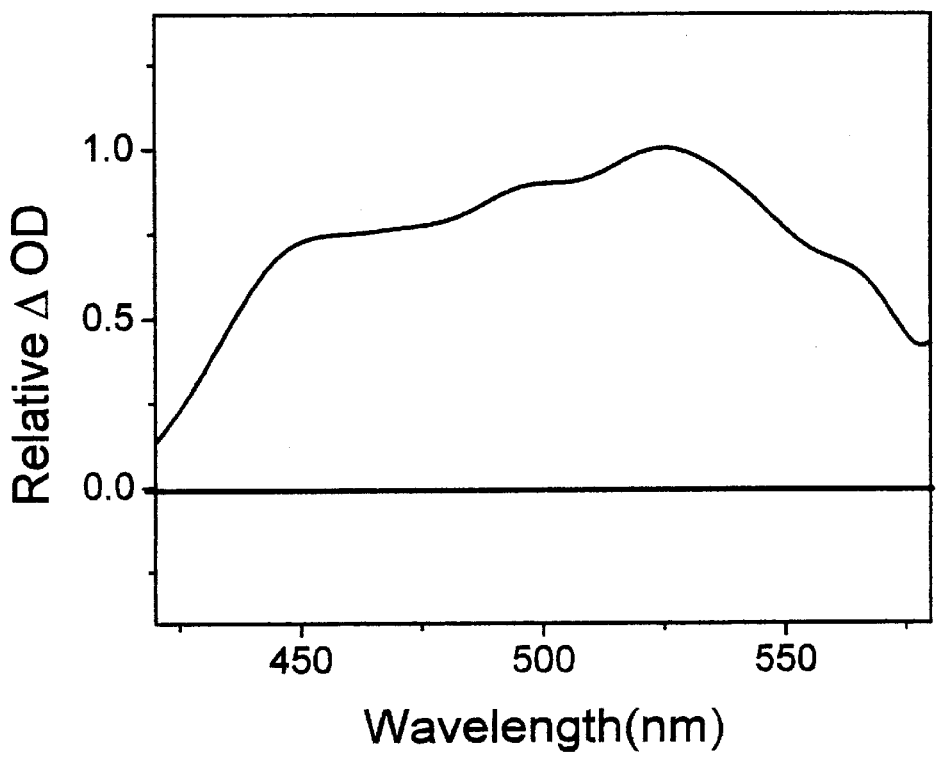
FIG. 2 is a graph depicting the increase in optical density as a function of wavelength for PbPc(PDMS$_{10}$)$_4$ after visible excitation.

These polysiloxane substituted phthalocyanine materials display an enhanced nonlinear optical absorption attributable to the phthalocyanine chromophore and the species complexed within the cavity. A reverse saturable absorption mechanism has been assigned to this photochemistry where an electronic transition from a first excited state to a second excited state has a higher transition probability than from the ground state to the first excited state. This transition from the first to the second excited state becomes the dominant transition once a threshold population is reached in the first excited state. To reach the critical first excited state population threshold, this state must have a sufficiently long lifetime. This long lifetime is promoted by having heavy metal ions complexed in the phthalocyanine cavity and by a low level of aggregation. Both the heavy metal ions and the polysiloxane peripheral groups are important influences in the current invention. FIG. 1 displays nonlinear transmission and optical limiting data of a 4.2 micron film of the phthalocyanine material of Example 5. These measurements were made at 532 nm using f/5 optics and an f/5 optical limiter with a pulse width of 7±1 ns. The sample transmission 532 nm was 84%. The nonlinear transmission measurements give an approximate excited state absorption cross-section of $1.0\pm0.2\times10^{-16}$ cm$^2$ and a ratio of the excited state to ground state extinction coefficient of 36 at this wavelength. This excited state absorption is larger than that found in solutions of PbPc(CP)$_4$, a known superior optical limiter (U.S. Pat. No. 5,805,326). The relative difference in absorption coefficients between the excited and ground states over a wavelength range of 430 to 600 nm following excitation at 606 nm for the phthalocyanine material of Example 5 is depicted in FIG. 2. This illustrates the wavelength window over which this material will be an effective optical limiter. Thus, FIG. 1 illustrates the magnitude of limiting for a single wavelength, and FIG. 2 shows a breadth of wavelengths where limiting will be effective.

Figure 3:
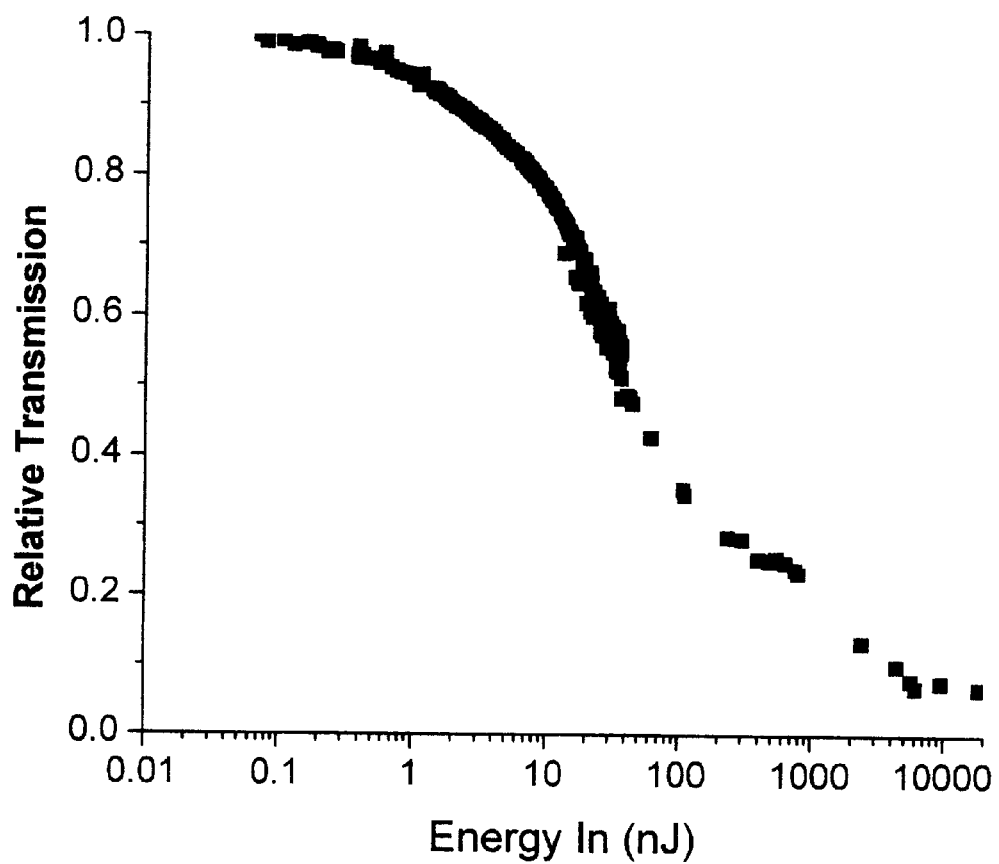
FIG. 3 is a graph demonstrating the optical limiting in f/5 optics for a 4.2 $\mu$m thick sample of pure liquid PbPc(PDMS$_{10}$)$_4$.

In addition to the nonlinear optical absorption of the phthalocyanine chromophore, the polysiloxane peripheral group makes a further contribution to the optical limiting through its nonlinear thermal refraction. A rapid change in refractive index with temperature, dn/dT, shifts the focal point of focused light and lowers the quantity of light passing through a series of focused optics. Because the phthalocyanine chromophore is very efficient in converting absorbed light to heat, a medium with a large refractive index response to heat will accentuate this thermal refractive effect. The polysiloxane structure has a very large refractive index response to heat, and by virtue of being bonded to the periphery of the phthalocyanine ring is well-positioned to accentuate this effect. The temperature dependence of the refractive index was measured for the polysiloxane phthalocyanine of Example 5 via ellipsometry to be $-5.4\pm1\times10^{-4\circ}$ C.$^{-1}$ between 25 and 40° C. and an average dn/dT of $-4\pm1\times10^{-4\circ}$ C.$^{-1}$ between 25 and 95° C. The latter value compares well with that found for linear polydimethylsiloxane liquids. Relative to other polymers, polydimethylsiloxane has an exceptionally large dn/dT. This thermal refractive enhancement to the optical limiting is depicted in FIG. 1 by comparing the optical limiting curve with that attributable to the only the nonlinear optical absorption. FIG. 3 shows the optical limiting measurements when carried to higher energies.

Other favorable properties that the polysiloxane peripheral groups confer on the phthalocyanine materials are chemical inertness and moisture resistance. The heavy metal ions, particularly lead, are labile to displacement from the phthalocyanine cavity. Competing complexing agents and the presence acid and moisture promote this displacement. As noted in the prior art description section, peripheral groups with coordination sites that will complex with a labile metal such as the polyethylene oxide structure can play the role of a competing complexing agent. Water and/or a source of protons complete the conversion to metal-free phthalocyanine. The oxygen atoms in the polysiloxane structure are very weak coordinating sites and are sterically hindered by pendant groups attached to the siloxane chain. The polysiloxane structure is also very hydrophobic. The lead phthalocyanine materials with peripheral siloxane substitution in the present invention are less labile than other lead phthalocyanine materials toward conversion to the metal-free analog.

EXAMPLES

The examples which follow serve to illustrate the practice of this invention and quantify the physical properties but are in no way intended to limit its application.

1. Synthesis and Characterization of Precursors

Example 1

Synthesis and Purification of 4-(2-allylphenoxy) phthalonitrile(I)

In a nitrogen atmosphere, 6.37 g (0.046 mol) of finely grounded anhydrous K$_2$CO$_3$ was added to a solution of 3.89 g (0.029 mol) of 2-allylphenol (Aldrich) and 5.02 g (0.029 mol) of 4-nitrophthalonitrile (Aldrich) in 25 mL of dry Me$_2$SO by 0.32 g additions at ½ h intervals over an 6-h period. The mixture was stirred 24 hours at room temperature under nitrogen. The undissolved salt is filtered from the reaction mixture and the filtrate is dissolved in 100 mL of methylene chloride. The solution is extracted 5 times with 50 mL water. The organic phase was dried over anhydrous magnesium sulfate, filtered and evaporated to dryness. The crude product is dissolved in minimum of toluene and chromatographed on alumina with toluene elution. The toluene was evaporated and the resulting oil vacuum dried to yield 5.28 g (70%) of I. The oil turns into a solid in few days.

$^1$H-RMN (CDCl$_3$, 300 MHz) 3.23 (2H, d, CH$_2$), 4.95 (2H, dd, =CH$_2$), 5.78 (1H, m, =CH), 6.95 (1H, d, Harom), 7.12–7.33 (5H, m, Harom), 7.68 (1H, d, Harom) ppm; $^{13}$C-RMN (CDCl$_3$, 75 MHz) 34.0, 108.5 114.9 and 115.4 (CN), 116.7, 117.6, 120.8, 120.9, 121.0, 126.7, 128.5, 131.6, 132.4, 135.3, 135.4, 151.1, 161.7 ppm; IR (NaCl) 3082 (=CH$_2$), 2229 (CN), 1615 (C=C), 1595 and 1486 (C—C), 1246 cm$^{-1}$.

Example 2

Synthesis and Purification of 4-(H$_9$C$_4$[Si(CH$_3$)$_2$O]$_9$Si(CH$_3$)$_2$(CH$_2$)$_3$C$_6$H$_4$O) Substituted Phthalonitrile (II)

A mixture of 1 g (3.84 mmol) of I and 4 drops of a 0.1 N isopropanol solution of H$_2$PtCl$_6$6H$_2$O (Aldrich) was heated at 60° C. Then 3 g (3.84 mmol) of hydrosilyl terminated PDMS precursor (H$_9$C$_4$[Si(CH$_3$)$_2$O]$_9$Si(CH$_3$)$_2$H) (A. T.

Holohan et al., *Macromol. Chem. Phys.* 195, 2965(1994)) were added dropwise. The mixture was stirred at 60° C. for 1 h. The oil obtained was purified by silica column chromatography using toluene as eluent. The solvent was evaporated to yield 2.20 g (55%) of a colorless oil after vacuum dry.

Tg: 14° C.; $n_D$=1.4482; $^1$H-RMN (CDCl$_3$, 300 MHz) 0.012–0.064 (60H,m, SiCH$_3$), 0.51 (4H), m, SiCH$_2$), 0.86 (3H, t, CH$_3$), 1.29 (4H, m, CH$_2$), 1.58 (2H, m, CH$_2$), 2.49 (2H, t, CH$_2$), 6.95 (1H, d, Harom), 7.14–7.31 (5H,m, Harom), 7.68 (1H, d, Harom) ppm; IR(NaCl) 2966 (CH), 2229 (CN), 1602 and 1492 (C—C) 1254 (SiCH$_3$), 1098 and 1033 (SiOSi), 806 (SiC) cm$^{-1}$.

Example 3

Synthesis and Purification of 4-(H$_9$C$_4$[Si(CH$_3$)$_2$O]$_{18}$Si(CH$_3$)$_2$(CH$_2$)$_3$C$_6$H$_4$O) Substituted Phthalonitrile (III)

The procedure is identical to that for example 2 except a longer hydrosilyl terminated PDMS precursor (H$_9$C$_4$[Si(CH$_3$)$_2$O]$_{18}$Si(CH$_3$)$_2$H) was used, in the same stoichiometric relationship.

Tg: 10° C.; $n_D$=1.4318; $^1$H-RMN (CDCl$_3$, 300 MHz) 0.015–0.144 (114H, m, SiCH$_3$), 0.54 (4H, m, SiCH$_2$), 0.88 (3H, t, CH$_3$), 1.32 (4H, m, CH$_2$), 1.55 (2H, m, CH$_2$), 2.50 (2H, t, CH$_2$), 6.95 (1H, d, Harom), 7.15–7.32 (5H, m, Harom), 7.70 (1H, d, Harom) ppm; IR (NaCl) 2966 (CH), 2235 (CN), 1608 and 1492 (C—C), 1272 (SiCH$_3$), 1098 and 1033 (SiOSi), 800 (SiC) cm$^{-1}$.

2. Synthesis and Characterization of Lead Phtahlocyanines

The procedure for lead phthalocyanine (Pc) is very similar and analogous to those reported by Lindstead and coworkers for unsubstituted metallophthalocyanines. The general reaction and purification were as follows except where departures are specified.

To a 10×75 mm tube fitted with a magnetic stifling bar were added the corresponding prescribed quantities of dicyano precursor (I, II, or III) and lead oxide (Fisher, yellow). The mixture was carefully fused under vacuum (less than 0.1 torr) to remove residual solvents and air occluded in the dicyano precursor and sealed under vacuum. The entire tube was heated with stirring for the designed time and temperature. The crude product was purified by column chromatography on silica (Fluka AG) using toluene as an elution solvent. The toluene was concentrated to yield a green liquid chromophore which was dried under vacuum at 80° C. for 2 h.

When dicyano precursor I was used, a green solid phthalocyanine was obtained which was purified by column chromatography on alumina (neutral Bodman, activity 1).

Example 4

PbPc(2-allylphenoxy)$_4$ (IV)

A mixture of 0.500 g (1.92 mmol) of I and 0.328 g (1.47 mmol) of PbO was reacted at 180° C. for 12 hours. Yield: 0.261 g (42%); m.p.>250° C.; UV-vis (toluene) 721, 650, 346 nm; IR(NaCl) 3076 (=CH$_2$), 2919 (CH), 1638 (C=C), 1608, 1485 (C—C), 1239 cm$^{-1}$.

Example 5

PbPc(OC$_6$H$_4$(CH$_2$)$_3$Si(CH$_3$)$_2$[O Si(CH$_3$)$_2$]$_9$C$_4$H$_9$)$_4$ (V)

A mixture of 0.800 g (0.766 mmol) of II and 0.131 g (0.589 mmol) of PbO was reacted at 180° C. for 12 hours. Yield: 0.512 g (61%); Tg: 3° C.; UV-vis (toluene) 721, 648, 365 nm; IR(NaCl) 2959 (CH), 1608 and 1492 (C—C), 1253 (SiCH$_3$), 1091 and 1014 (SiOSi), 800 (SiC) cm$^{-1}$. Phthalocyanine V can also be prepared by hydrosilylation reaction over the phthalocyanine IV. A mixture of 0.100 g (0.077 mmol) of IV and 8 drops of Platinum divinyltetramethyldisiloxane complex in xylene (Gelest Inc) was dissolved in 2 mL of toluene and was heated at 60° C. Then 0.481 g (0.616 mmol) of hydrosilyl terminated PDMS precursor (H$_9$C$_4$[Si(CH$_3$)$_2$O]$_9$Si(CH$_3$($_2$H) were dropwise added. The mixture was stirred at 60° C. for 6 h. and purified in the same way.

Example 6

PbPc(OC$_6$H$_4$(CH$_2$)$_3$Si(CH$_3$)$_2$[OSi(CH$_3$)$_2$]$_{18}$C$_4$H$_9$)$_4$ (VI)

A mixture of 0.500 g (0.292 mmol) of III and 0.050 g (0.224 mmol) of PbO was reacted at 180° C. for 12 hours. Yield: 0.226 g (44%); Tg: 10° C.; WV-vis (toluene) 719, 647, 389, 367 nm; v(NaCl) 2966 (CH), 1621 and 1486 (C—C), 1266 (SiCH$_3$), 1091 and 1033 (SiOSi), 800 (SiC) cm$^{-1}$.

3. Synthesis and Characterization of Metal Free Phtahlocyanines

Example 7

H$_2$Pc(2-allylphenoxy)$_4$ (VII)

To a 10×75 mm tube fitted with a magnetic stirring bar were added 0.500 g (1.92 mmol) of I and 0.052 g (0.48 mmol) of hydroquinone (Aldrich). The mixture was carefully fused under vacuum (less than 0.1 torr) to remove residual solvents occluded in the dicyano precursor and sealed under vacuum. The entire tube was heated at 170° C. with stirring for 12 h. The crude product was purified by column chromatography on alumina (neutral Bodman, activity 1) using toluene as an elution solvent. The toluene was concentrated and the blue solid obtained was dissolve in a minimum amount of chloroform, and the phthalocyanine was precipitated by dropwise addition of methanol. The product was collected and dried. Yield: 0.280 g (56%); m.p.>250° C.; UV-vis (toluene) 703, 667, 639, 605, 350 nm; IR(NaCl)3295 (NH), 3075 (=CH$_2$), 1638 (CH=CH$_2$), 1611 and 1467(C—C), 1228 cm$^{-1}$;

$^1$H-RMN (CDCl$_3$, 300 MHz) −4.1 (s, NH), 3.6 (m, CH$_2$), 5.1 (m, =CH$_2$), 6.1 (m, CH=), 6.8–7.7 (m, Harom) ppm; m/z 1091.

Example 8

H$_2$Pc(OC$_6$H$_4$(CH$_2$)$_3$Si(CH$_3$)$_2$[OSi(CH$_3$)$_2$]$_9$C$_4$H$_9$)$_4$ (VIII)

Metal free phthalocyanine VIII was obtained by displacement of a lead ion from the phthalocyanine (V).

To a solution of 0.300 g (0.068 mmol) of V in 10 mL of methylene chloride were added three drops of trifluoroacetic acid. The mixture was stirred at room temperature for 10 min. The methylene chloride solution was extracted 3 times with 15 mL of 5% NaHCO$_3$. The organic phase was dried over anhydrous magnesium sulfate, filtered and evaporated to dryness. The crude product was purified by column chromatography on silica (Fluka AG) using toluene as an elution solvent. The toluene was concentrated to yield a blue liquid which was dried under vacuum at 80° C. for 2 h. Yield: 0.160mg (56%); Tg: 6° C.; UV-vis (toluene) 703, 666, 638, 605, 346 nm; IR(NaCl) 3295 (NH), 2959 (CH), 1615 and 1479 (C—C), 1259 (SiCH$_3$), 1091 and 1027 (SiOSi), 807 (SiC) cm$^{-1}$; m/z 4500–2200.

Compound VIII may also be prepared following a similar procedure to those reported by O. Bekarôglu and co-workers (A. G. Gurek, O. Bekarôglu, *J. Chem. Soc. Dalton Trans.*, 1994, 1419).

A mixture of 0.250 g (0.24 mmol) of II and 0.036 g (0,24 mmol) of DBU (1,8-diazabicyclo[5.4.0]undec-7-ene) (Aldrich) was dissolved in 2 mL of pentan-1-ol. The mixture was stirred at 136° C. for 7 h. The solvent was removed by vacuum distillation and the crude was purified as above.

Obviously, many modifications and variations of the present invention are possible in light of the above teachings. Additional advantages and modifications will readily occur to those skilled in the art. Therefore, the invention in its broader aspects is not limited to only the specific details and representative embodiments shown and described herein. Accordingly, various modifications may be made without departing from the spirit or scope of the general inventive concept as defined by the appended claims and their equivalents.

What is claimed is:

1. A phthalocyanine compound with peripheral siloxane substitution on the benzo ring substructures having the structure:

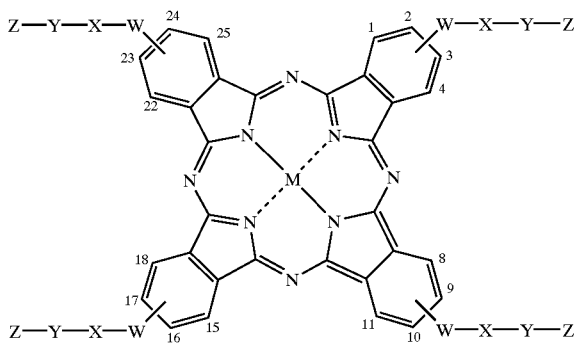

wherein
—W—X—Y—Z are peripheral groups comprising individual W, X, Y, and Z subgroups, wherein W is covalently bonded to any of the numbered positions on the benzo ring sub-structures, and where each of said benzo ring substructures may have 0, 1, or 2 of said —W—X—Y—Z peripheral groups;

W is a linkage represented by the formula: —D—(R$^1$)$_{0,1}$—, where D is an atom selected from the group consisting of sulphur and oxygen; and R$^1$ is a intermediary selected from the group consisting of aryl and alkyl hydrocarbons;

X is: —(CH$_2$)$_n$—, n=2 to 8;

Y is a siloxane chain having the formula:

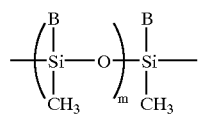

m=3 to 100

B is a pendant substituent selected from the group consisting of —C$_p$H$_{2p+1}$, where p=1 to 4; —C$_6$H$_5$; —CH$_2$CH$_2$CF$_3$; and combinations thereof;

Z is a terminal cap on the free end of the W—X—Y—Z peripheral groups selected from the group consisting of —H; linear alkyl group represented by the formula —C$_q$H$_{2q+1}$, where q=1 to 8; branched alkyl group represented by the formula —C$_q$H$_{2q+1}$, where q=1 to 8; and an aryl group; and M is two protons or a metal ion.

2. The phthalocyanine compound of claim 1, wherein each said benzo ring substructure has one of said —W—X—Y—Z peripheral groups attached.

3. The phthalocyanine compound of claim 2, wherein each said —W—X—Y—Z peripheral group is attached at a different peripheral ring position on each said benzo ring substructure.

4. The phthalocyanine compound of claim 1, wherein said metal ion is an element selected from the group consisting of Pb, Sn, Bi, In, Tl, Cd, Si, Zn, and Hg.

5. The phthalocyanine compound of claim 1, wherein said metal ion is Pb.

6. The phthalocyanine compound of claim 1, wherein said (R$^1$)$_{0,1}$ is (R$^1$)$_0$.

7. The phthalocyanine compound of claim 1, wherein said (R$^1$)$_{0,1}$ is:

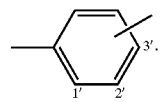

8. The phthalocyanine compound of claim 7, wherein said X subgroup is attached to said R$^1$ portion of said peripheral group W at the 1' position.

9. The phthalocyanine compound of claim 1, wherein said X subgroup is a trimethylene group.

10. The phthalocyanine compound of claim 1, wherein said pendant substituent B is a methyl group.

11. The phthalocyanine compound of claim 1, wherein said terminal cap Z is either a branched or linear inert alkyl group having the formula —C$_q$H$_{2q+1}$, where q=1 to 8.

12. The phthalocyanine compound of claim 1, wherein said Y subgroup is a siloxane chain ranging in length from 7 to 28 units.

13. A method of making the phthalocyanine compound of claim 1, comprising the steps of:
(a) anionically polymerizing a solution of cyclotrisiloxane monomers by addition of an alkyl lithium initiator and a dimethylchlorosilane termination reagent, thereby forming a silylhydride terminated siloxane polymer;
(b) performing a nucleophilic aromatic nitro displacement reaction between a mixture of an inorganic base, a nitrophthalonitrile, and a terminal olefin substituted alcohol or thiol to obtain an olefin terminated alkyl substituted phthalonitrile intermediate;
(c) performing a hydrosilylation coupling reaction between said terminated alkyl substituted phthalonitrile intermediate, said silylhydride terminated siloxane polymer, and a hydrosilylation catalyst to form a polysiloxane substituted phthalonitrile intermediate; and
(d) converting of said polysiloxane substituted phthalonitrile intermediate to said phthalocyanine compound with peripheral siloxane substitution on the benzo ring substructures.

14. The method as recited in claim 13, wherein said inorganic base is potassium carbonate.

15. The method as recited in claim 13, wherein said nitrophthalonitrile has the nitro group substituted at the number 3 position.

16. The method as recited in claim 13, wherein said nitrophthalonitrile has the nitro group substituted at the number 4 position.

17. The method as recited in claim 13, wherein said terminal olefin substituted alcohol is a terminal olefin substituted alkyl phenol.

18. The method as recited in claim 17, wherein said terminal olefin substituted alkyl phenol is 2-allylphenol.

19. The method as recited in claim 13, wherein said olefin terminated alkyl substituted phthalonitrile intermediate is 4-(2'-allylphenoxy)phthalonitrile.

20. The method as recited in claim 13, wherein said step of conversion to said phthalocyanine compound with peripheral siloxane substitution on the benzo ring substructures is accomplished by reacting said polysiloxane substituted phthalonitrile intermediate with a mixture of 1,8-diazabicyclo[5.4.0]undec-7-ene (DBU) and pentanol.

21. The method as recited in claim 13, wherein said step of conversion to said phthalocyanine compound with peripheral siloxane substitution on the benzo ring substructures is accomplished by reacting said polysiloxane substituted phthalonitrile intermediate with a mixture of dimethylaminoethanol and a metal salt.

22. The method as recited in claim 13, wherein said step of conversion to said phthalocyanine compound with peripheral siloxane substitution on the benzo ring substructures is accomplished by reacting said polysiloxane substituted phthalonitrile intermediate with lead (II) oxide to obtain a lead phthalocyanine compound with peripheral siloxane substitution on the benzo ring substructures.

23. The method as recited in claim 22, further comprising the step of treating said lead phthalocyanine with trifluoroacetic acid to yield a metal-free form of said phthalocyanine compound with peripheral siloxane substitution on the benzo ring substructures.

24. The method as recited in claim 23, further comprising the step of treating said metal-free phthalocyanine compound with a solution of a basic salt of a metal to yield a metallic chromophore in said phthalocyanine compound with peripheral siloxane substitution on the benzo ring substructures.

25. The method as recited in claim 24, wherein said metal is selected from the group consisting of Sn, Bi, In, Tl, Cd, Si, Zn, and Hg.

26. The method as recited in claim 13, wherein said hydrosilylation catalyst is chloroplatinic acid.

27. A method of making the phthalocyanine compound of claim 1, comprising the steps of:
  (a) anionically polymerizing a solution of cyclotrisiloxane monomers by addition of an alkyl lithium initiator and a dimethylchlorosilane termination reagent, thereby forming a silylhydride terminated siloxane polymer;
  (b) performing a nucleophilic aromatic nitro displacement reaction between a mixture of potassium carbonate, a nitrophthalonitrile, and terminal olefin substituted alcohol to obtain an olefin terminated alkyl substituted phthalonitrile intermediate;
  (c) converting said olefin terminated alkyl substituted phthalonitrile intermediate by mixing with lead (II) oxide thereby forming its corresponding tetraolefin terminated alkyl substituted phthalocyanine; and
  (d) performing a hydrosilylation coupling reaction between said tetraolefin terminated alkyl substituted phthalocyanine, said silylhydride terminated siloxane polymer, and a non-acidic hydrosilylation coupling catalyst to form said phthalocyanine compound with peripheral siloxane substitution on the benzo ring substructures.

\* \* \* \* \*